(12) United States Patent
Chen et al.

(10) Patent No.: US 9,885,801 B2
(45) Date of Patent: Feb. 6, 2018

(54) DETECTOR DEVICE, DUAL ENERGY CT SYSTEM AND DETECTION METHOD USING THE SYSTEM

(71) Applicants: Tsinghua University, Beijing (CN); Nuctech Company Limited, Beijing (CN)

(72) Inventors: Zhiqiang Chen, Beijing (CN); Li Zhang, Beijing (CN); Xin Jin, Beijing (CN); Qingping Huang, Beijing (CN); Le Shen, Beijing (CN); Yunda Sun, Beijing (CN)

(73) Assignees: TSINGHUA UNIVERSITY, Beijing (CN); NUCTECH COMPANY LIMITED, Beijing (CN)

( * ) Notice: Subject to any disclaimer, the term of this patent is extended or adjusted under 35 U.S.C. 154(b) by 0 days.

(21) Appl. No.: 14/748,407

(22) Filed: Jun. 24, 2015

(65) Prior Publication Data

US 2015/0378047 A1 Dec. 31, 2015

(30) Foreign Application Priority Data

Jun. 25, 2014 (CN) .......................... 2014 1 0291326

(51) Int. Cl.
*G01T 1/202* (2006.01)
*A61B 6/00* (2006.01)
(Continued)

(52) U.S. Cl.
CPC ............ *G01V 5/0041* (2013.01); *G01T 1/362* (2013.01); *G01T 7/08* (2013.01); *G01V 5/005* (2013.01); *A61B 6/4266* (2013.01); *G01T 1/202* (2013.01)

(58) Field of Classification Search
None
See application file for complete search history.

(56) References Cited

U.S. PATENT DOCUMENTS

| 5,841,833 A | 11/1998 | Mazess et al. |
| 7,778,383 B2 | 8/2010 | Koehler et al. |
| 8,831,305 B2 | 9/2014 | Zhang et al. |

(Continued)

FOREIGN PATENT DOCUMENTS

| CN | 101410727 A | 4/2009 |
| CN | 101900695 A | 12/2010 |

(Continued)

OTHER PUBLICATIONS

European Patent Office Communication dated Jun. 26, 2017 for European application No. 15 173 496.9-1559.

(Continued)

*Primary Examiner* — Jason McCormack
*Assistant Examiner* — James Choi
(74) *Attorney, Agent, or Firm* — Browdy and Neimark, P.L.L.C.

(57) ABSTRACT

The present disclosure discloses a detector device comprising a plurality of detector assemblies. Each detector assembly comprises at least one detection crystal units having a first energy response and those having a second energy response, which are both arranged along a first direction at intervals, each detection crystal unit having a first/second energy response including at least one detection crystals having a first/second energy response arranged along a second direction. The at least one detection crystal units having a first energy response and the at least one detection crystal units having a second energy response are, at least partially, alternatively arranged along the first direction when viewed from an incidence direction of the X-ray. The present disclosure also discloses a dual energy CT system having the detector device and a CT detection method using this system.

10 Claims, 4 Drawing Sheets

(51) Int. Cl.
*G01T 1/36* (2006.01)
*G01V 5/00* (2006.01)
*G01T 7/08* (2006.01)

(56) References Cited

U.S. PATENT DOCUMENTS

| | | | |
|---|---|---|---|
| 9,176,078 B2 | 11/2015 | Flohr et al. | |
| 9,572,540 B2 | 2/2017 | Zhang et al. | |
| 2007/0003006 A1* | 1/2007 | Tkaczyk | G01T 1/2985 378/19 |
| 2010/0220833 A1* | 9/2010 | Levene | G01T 1/2018 378/19 |
| 2012/0025086 A1 | 2/2012 | Takihi | |
| 2012/0236987 A1* | 9/2012 | Ruimi | A61B 6/032 378/19 |
| 2013/0256538 A1* | 10/2013 | Vogtmeier | G01T 1/2006 250/366 |
| 2014/0314200 A1 | 10/2014 | Chen et al. | |
| 2014/0376686 A1* | 12/2014 | Dreiseitel | G01V 5/005 378/5 |
| 2016/0274249 A1* | 9/2016 | Vogtmeier | G01T 1/2018 |
| 2017/0120076 A1* | 5/2017 | Allinson | A61N 5/1071 |

FOREIGN PATENT DOCUMENTS

| | | | |
|---|---|---|---|
| CN | 202948145 U | | 5/2013 |
| CN | 103674979 A | | 3/2014 |
| CN | 103675931 A | | 3/2014 |
| CN | 103705267 A | | 4/2014 |
| GB | 2496777 A | | 1/2013 |
| JP | 04230899 A | * | 8/1992 |
| JP | 2010-190830 A | | 9/2010 |
| JP | 2012-518782 A | | 8/2012 |
| WO | 2009073284 A | | 6/2009 |
| WO | 2014044078 A | | 3/2014 |
| WO | 2014048163 A | | 4/2014 |

OTHER PUBLICATIONS

JPO Office Action for Japanese Patent Application No. 2015-127599, dated Feb. 8, 2017 (with English Translation).

Office Action Issued in SIPO, Chinese Patent Application No. 20140291326, dated Apr. 1, 2017 (with Machine Translation into English).

* cited by examiner

Fig. 4

DETECTOR DEVICE, DUAL ENERGY CT SYSTEM AND DETECTION METHOD USING THE SYSTEM

CROSS-REFERENCE TO RELATED APPLICATION

This application claims the benefit of Chinese Patent Application No. 201410291326.4 filed on Jun. 25, 2014 in the State Intellectual Property Office of China, the whole disclosure of which is incorporated herein by reference.

BACKGROUND OF THE INVENTION

Field of the Invention

The present disclosure relates to the technical field of dual energy CT detection, in particular, relates to a detector device for a dual energy CT system, a dual energy CT system including the detector device and a detection method using the dual energy CT system.

Description of the Related Art

At present, a computer tomography technology (hereinafter referred to as CT technology) based on X-ray radiation imaging is widely used for security inspection, in particular, for inspecting suspicious articles in baggage. In the CT scanning technology based on X-ray radiation imaging, data for characteristic distribution of an object to be scanned in the tomography imaging is obtained by CT data reconstruction. Analysis of such characteristic data contributes to identification of common suspect substance in the baggage. A conventional CT apparatus includes an X-ray source, a collimating device, a rotatable slip-ring, detection units, a dedicated computer system for data calculation, power and control subsystems, etc.

In a conventional dual energy CT structure, the detection unit usually comprises detection crystal units having different energy responses, that is, detection crystal units having a first energy response (e.g., low energy detection crystal units) and detection crystal units having a second energy response (e.g., high energy detection crystal units). Usually, the number of the detection crystal units having a first energy response is equal to that of the detection crystal units having a second energy response. The two types of detection crystal units are provided on two sides of a printed circuit board, respectively. When viewed from incidence direction of the ray, the two types of detection crystal units are aligned with each other (i.e., overlapped) with the printed circuit board being sandwiched therebetween, and the respective detection crystal units having a first energy response corresponds to the respective detection crystal units having a second energy response. During detection, an acquisition module is used to acquire data signals from the detection units, and the acquired data signals are decomposed into data from the detection crystal units having a first energy response and data from the detection crystal units having a second energy response by a dual energy decomposition technology, so as to reconstruct attenuation coefficient images, electron density images and atomic number images of the object in X-ray scanning with different energies. In this way, substance components can be identified and prohibited substance, such as drugs, explosives or the like, can be detected.

For dual energy CT security inspection, sharpness of three-dimension images and identification accuracy of substance are key factors for imaging. However, these two factors require the detector units in different ways. In order to improve sharpness of three-dimension images, it is necessary to increase the number of the detection crystal units having a first energy response or the detection crystal units having a second energy response. However, in order to improve identification accuracy of substance, it is necessary to increase the numbers of the detection crystal units having a first energy response and of the detection crystal units having a second energy response. Furthermore, the number of crystals required for improving sharpness of three-dimension images is much greater than the number of crystal required for improving identification accuracy of substance.

Therefore, in respect that detector crystals are expensive, it is desired to optimize an overall cost of a detector and to ensure a high spatial resolution for CT image reconstruction while meeting requirements for identification accuracy of substance.

SUMMARY OF THE INVENTION

In view of the above, the present disclosure aims to solve at least one of the above-mentioned problems and defects existing in the prior art.

An object of the present disclosure is to provide a novel detector device for a dual energy CT system, which has such an arrangement that detection crystal units having a first energy response and detection crystal units having a second energy response are alternatively disposed, so that optimization of detection cost can be realized, and a high spatial resolution for CT image reconstruction can be ensured while meeting requirements for identification accuracy of scanned substance. This detector device may be used to inspect suspicious objects in baggage.

According to an aspect of the present disclosure, there is provided a detector device for a dual energy CT system, wherein the dual energy CT system comprises a scanning tunnel through which objects to be scanned (e.g., baggage) enter/exit the dual energy CT system along a transporting direction, an X-ray source provided at a side of the scanning tunnel, and a gantry provided at an opposite side of the scanning tunnel and on which the detector device is mounted, and wherein the detector device comprises a plurality of detector assemblies, each detector assembly comprising:

at least one detection crystal units having a first energy response (e.g., low energy detection crystal units) which are arranged along a first direction at intervals, each detection crystal unit having a first energy response including at least one detection crystals having a first energy response arranged along a second direction, wherein the first direction is parallel to the transporting direction, and the second direction is perpendicular to the first direction; and at least one detection crystal units having a second energy response (e.g., high energy detection crystal units) which are arranged along the first direction at intervals, each detection crystal unit having a second energy response including at least one detection crystals having a second energy response arranged along the second direction, wherein the second energy is higher than the first energy;

wherein the at least one detection crystal units having a first energy response and the at least one detection crystal units having a second energy response are, at least partially, alternatively arranged along the first direction when viewed from an incidence direction of the X-ray.

It should be noted that the feature or disclosure of "the second energy is higher than the first energy" described throughout means "the second equivalent (or average) energy corresponding to the second energy response is higher than the first equivalent (or average) energy corresponding to the first energy response".

With the detector device according to the present disclosure, since the detection crystal units having a first energy response and the detection crystal units having a second energy response are, at least partially, alternatively arranged (i.e., are arranged not to be aligned) along the first direction, in a mode of single energy processing, the spatial sampling locations for detecting the X-ray are increased, compared to the conventional arrangement in which the detection crystal units having a second energy response and the detection crystal units having a first energy response are arranged to be aligned with each other. A part of the X-ray emitted from the X-ray source is acquired by either of the detection crystal units having a first energy response and the detection crystal units having a second energy response that are alternatively arranged, and the rest of the X-ray is acquired by the detection crystal units having a first energy response and the detection crystal units having a second energy response that are aligned with each other. Then, all the acquired data signals are used for CT image reconstruction of the scanned object, so that spatial resolution can be enhanced. Furthermore, since the number of the detection crystal units having a second energy response are not increased, manufacturing cost for the detector device will not be increased significantly.

In a specific embodiment, the number of the detection crystal units having a first energy response is equal to that of the detection crystal units having a second energy response.

Further, since difference in manufacturing cost between the detection crystals having a first energy response and the detection crystals having a second energy response is great, when the cost of the detection crystals having a first energy response is much lower than that of the detection crystals having a second energy response, the number of the detection crystal units having a first energy response may be greater than that of the detection crystal units having a second energy response. Therefore, the spatial resolution for CT image reconstruction can be enhanced by increasing the number of the detection crystal units having a first energy response, without increasing the manufacturing cost of the detector device significantly.

Further, the at least one detection crystal units having a first energy response and the at least one detection crystal units having a second energy response are arranged along the first direction in an entirely alternative arrangement (i.e., the two types of detection crystal units are not aligned with each other in the first direction). Such arrangement means that in the mode of single energy processing, the spatial sampling locations for X-ray detection are further increased by alternatively arranging all the detection crystal units having a first energy response and a second energy response, without changing the total number of the detection crystal units (i.e., without increasing the total manufacturing cost).

In an embodiment, the plurality of detector assemblies are arranged on a circular arc-shaped support centered at a center of the scanning tunnel or on an approximate circular arc-shaped support consisting of a plurality of straight members and centered at the center of the scanning tunnel. Specifically, the detector assemblies of the detector device for the dual energy CT system described in the present disclosure may be arranged in the arrangement disclosed in the Chinese Patent Application No. 201210350516.X (title: CT SECURITY INSPECTION SYSTEM FOR BAGGAGE AND DETECTOR ARRANGEMENT THEREOF).

Alternatively, the plurality of detector assemblies may be arranged on a circular arc-shaped support centered at the X-ray source or an approximate circular arc-shaped support consisting of a plurality of straight members.

Alternatively, the plurality of detector assemblies may be arranged on the circular arc-shaped or approximate circular arc-shaped support in a spiral manner, so that a detection path for detecting the scanned object is a spiral path when the scanned object is transported to pass through a scanning plane.

In a preferred embodiment, incidence surfaces of the detection crystal units having a first energy response and/or the detection crystal units having a second energy response may be provided thereon with filtering layers for adjusting energy response of the detection crystal units.

In a preferred embodiment, the detector device further comprises a mounting plate. The detection crystal units having a first energy response are arranged on a side of the mounting plate in such manner that the detection crystal units having a first energy response are arranged along the first direction at intervals, and the detection crystal units having a second energy response are arranged on the other side of the mounting plate in such manner that the detection crystal units having a second energy response are arranged along the first direction at intervals.

In another preferred embodiment, the at least one detection crystal units having a first energy response and the at least one detection crystal units having a second energy response are mounted on the same or different sides of different mounting plates.

Preferably, the X-ray source is a single light source or a distributed multi-beam source.

According to another aspect of the present disclosure, there is provided a detector device for a dual energy CT system. The detector device comprises a plurality of detector assemblies. Each detector assembly comprises at least two detection crystal units having a first energy response arranged along the first direction at intervals, and each detection crystal unit having a first energy response comprises at least one detection crystals having a first energy response arranged along the second direction. The first direction is parallel to the transporting direction of the scanned object. The second direction is perpendicular to the first direction. The detector assembly also comprises at least one detection crystal units having a second energy response arranged along the first direction at intervals, and each detection crystal unit having a second energy response comprises at least one detection crystals having a second energy response arranged along the second direction. The second energy is higher than the first energy. The number of the detection crystal units having a second energy response is less than that of the detection crystal units having a first energy response. When viewed from an incidence direction of the X-ray, some of the at least two detection crystal units having a first energy response correspond to and are arranged to be aligned with respective detection crystal units of the at least one detection crystal units having a second energy response.

As described above, since the cost of the detection crystal having a first energy response (e.g., the low energy detection crystal) is much lower than that of the detection crystal having a second energy response (e.g., the high energy detection crystal), sharpness of three-dimension images can be enhanced by increasing the number of the detection crystal units having a first energy response. Meanwhile, since the number of the detection crystals required for meeting accuracy requirements of substance identification is much less than the number of the detection crystals required for meeting sharpness requirements of three-dimension images, a small amount of the detection crystal units having a second energy response can be provided. Thus, detection cost can be optimized, and a higher spatial resolution for CT image reconstruction can be ensured while meeting accuracy requirements of substance identification.

According to a further aspect of the present disclosure, there is provided a dual energy CT system, comprising a scanning tunnel through which an object to be scanned, such as baggage, enters and exits the dual energy CT system along a transporting direction, an X-ray source provided at a side of the scanning tunnel, and a gantry provided at an opposite side of the scanning tunnel. The above-described detector device is mounted on the gantry.

In an embodiment, the dual energy CT system further comprises an acquisition module for acquiring data signals from the plurality of detector assemblies and a control module for controlling radiation emission of the X-ray source and the data signal acquisition operation, and the control module and the acquisition module are mounted within the same gantry.

In an embodiment, the dual energy CT system according to the present disclosure further comprises a data processing module. The data processing module is configured to perform a first data processing and a second data processing. In the first data processing, a single energy processing mode is used, and all the acquired data signals are used to reconstruct CT images of the scanned object. In the second data processing, a dual energy processing mode is used, and the acquired data signals are decomposed into data signals from the at least one detection crystal units having a first energy response and data signals from the at least one detection crystal units having a second energy response. Then, the decomposed data signals are used for reconstruction to obtain attenuation coefficient images, electron density images and atomic number images of the scanned article in X-ray scanning with different energies.

In a specific embodiment, the data processing module may be configured to, in the second data processing, employ interpolation algorithms to obtain dual energy projection data which correspond to an alignment arrangement and then perform reconstruction of attenuation coefficient images, electron density images and atomic number images in X-ray scanning with different energies in the case where the detection crystal units having a second energy response and the detection crystal units having a first energy response are alternatively arranged. With such configuration, the problem that the dual energy decomposition cannot be directly realized due to misalignment of the detection crystal units having a first energy response and a second energy response can be solved.

According to a further aspect, there is provided a CT detection method using the above-described dual energy CT system, comprising the steps of: transporting the object to be scanned (e.g., baggage) through the scanning tunnel; driving the gantry to rotate and at the same time controlling the X-ray source to emit the X-ray; acquiring data signals from the plurality of detector assemblies; and performing a first data signal processing and a second data signal processing, wherein in the first data processing, a single energy processing mode is used, and the acquired data signals are used to reconstruct CT images of the scanned object, and in the second data processing, a dual energy processing mode is used, and the acquired data signals are decomposed into data signals from the at least one detection crystal units having a first energy response and data signals from the at least one detection crystal units having a second energy response. Then, the decomposed data signals are used for reconstruction to obtain the attenuation coefficient images, the electron density images and the atomic number images of the scanned article in X-ray scanning with different energies.

In a preferred embodiment, in the second data processing, interpolation algorithms is employed to obtain dual energy projection data which correspond to an alignment arrangement and then perform reconstruction of the attenuation coefficient images, the electron density images and the atomic number images in X-ray scanning with different energies in the case where the detection crystal units having a second energy response and the detection crystal units having a first energy response are alternatively arranged.

BRIEF DESCRIPTION OF THE DRAWINGS

The above and other features of the dual energy CT system and the detector assemblies used in the same according to the present disclosure will become more apparent by describing in detail exemplary embodiments thereof with reference to the accompanying drawings by way of examples. Throughout the drawings, same reference numerals represent same or similar members.

DETAILED DESCRIPTION OF PREFERRED EMBODIMENTS OF THE INVENTION

Embodiments of the present disclosure will be further explained below with reference to the accompanying drawings. It should be noted that same or similar reference numerals represent same or similar members or those having same or similar functions. The following embodiments are only explained by way of examples, instead of being intended to limit the scope of the present invention.

Figure 1:
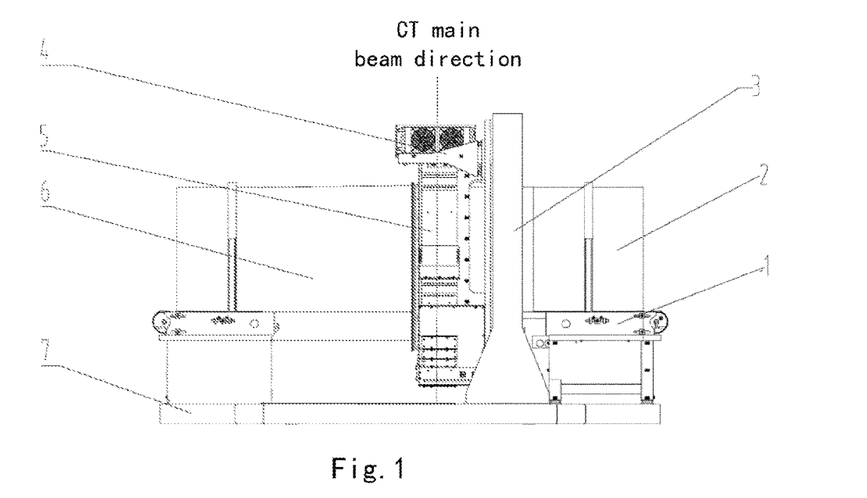
FIG. 1 is a schematic view of an overall dual energy CT system according to an embodiment of the present disclosure.

Referring to FIG. 1, it shows a dual energy CT (computer tomography) system according to an exemplary embodiment of the present disclosure. Such system may be used for inspecting suspicious articles, for example, in baggage. The dual energy CT system comprises a scanning entrance tunnel 2 and a scanning exit tunnel 6 through which an object to be scanned (not shown), such as baggage, enters and exits the dual energy CT system along a transporting direction shown at arrow A, an X-ray source 8 provided between the scanning entrance tunnel 2 and the scanning exit tunnel 6, a gantry 5 provided at an opposite side to the X-ray source 8. A detector device 20 is mounted on the gantry 5, and the detector device 20 comprises a plurality of detector assemblies 21. In one preferred embodiment, the dual energy CT system further comprises a slip-ring subsystem 3 disposed around the scanning tunnel, and the X-ray source 8 and the gantry 5 are mounted on the slip-ring subsystem 3 and are rotatable about the center of the scanning tunnel.

Figure 2:
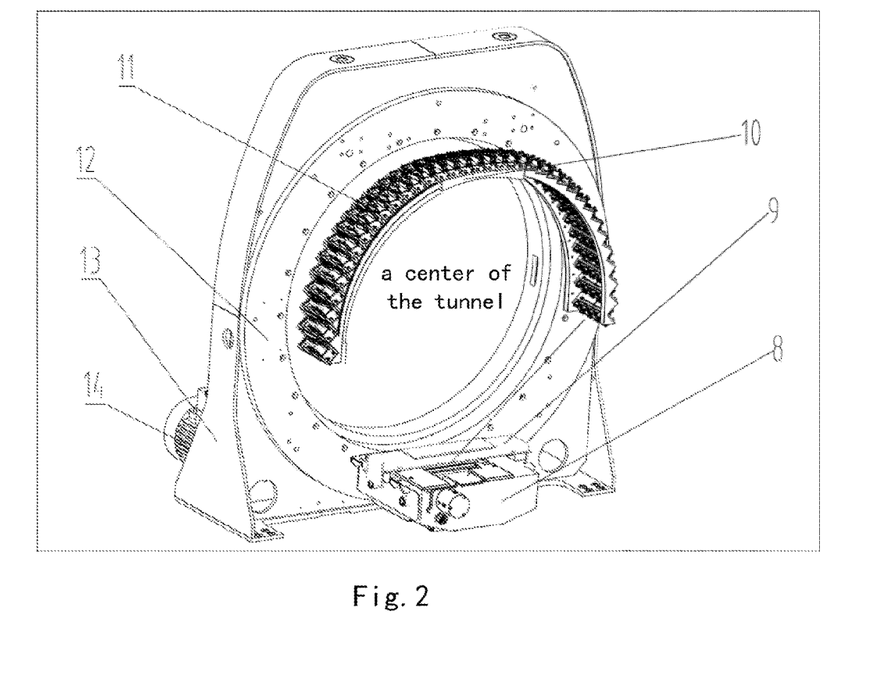
FIG. 2 is a schematic perspective view of main components of the dual energy CT system.

As shown in FIG. 2, in the above-mentioned CT system, the gantry 5 is mounted on a rotatable gantry-mounting plate 12 of the slip-ring subsystem 3 for mounting the gantry 5, and the gantry-mounting plate 12 is mounted in slip-ring supporting frame 13 and is driven by a slip-ring driving motor 14. Also, the detector device 20, the X-ray source 8, a first collimator 9 and a second collimator 10 are mounted on the gantry 5. In this embodiment, there is only one gantry 5 in this system. The gantry 5 is a closed structure in which a data acquisition/control module 34 is mounted. The whole CT data acquisition system can employ a set of data acquisition module and control module. Further, all the acquired data can be processed by one type of algorithm, so that a speed for performing a scanning operation in the CT system can be increased and a data transferring and processing speed can also be increased.

Referring to FIGS. 3(a)-(d), exemplary arrangements of detection crystal units 22 having a first energy response and detection crystal units 23 having a second energy response in the detector assembly 21 of the detector device 20 according to the present disclosure are illustratively shown. In an embodiment, the detection crystal unit having a first energy response is a low energy detection crystal unit consisting of at least one low energy detection crystal, and the detection crystal unit having a second energy response is a high energy detection crystal unit consisting of at least one high energy detection crystal. According to the present disclosure, each detector assembly 21 comprises at least one detection crystal units 22 having a first energy response arranged along a first direction (as shown at arrow B) at intervals, and each detection crystal unit 22 having a first energy response comprises at least one detection crystals 22a, 22b, 22c . . . having a first energy response arranged along a second direction. The second direction (as shown at arrow C) is perpendicular to the first direction. The detector assembly 21 also comprises at least one detection crystal units 23 having a second energy response arranged along the first direction at intervals, and each detection crystal unit 23 having a second energy response comprises at least one detection crystals 23a . . . having a second energy response arranged along the second direction. The second energy is higher than the first energy. When viewed from an incidence direction of the X-ray, the at least one detection crystal units 22 having a first energy response and the at least one detection crystal units 23 having a second energy response are, at least partially, alternatively arranged along the first direction. For instance, one detection crystal unit having a first energy response and one detection crystal unit having a second energy response are alternatively arranged along the first direction and are not aligned with each other.

One skilled in the art of detection using detection crystals can understand that the feature or disclosure of "the second energy is higher than the first energy" described herein substantively means "the second equivalent (or average) energy corresponding to the second energy response is higher than the first equivalent (or average) energy corresponding to the first energy response". In other words, the feature or disclosure of "the second energy is higher than the first energy" described herein substantively relates to comparison of equivalent energies or average energies corresponding to the respective energy responses.

With such detector device, since the detection crystal units 22 having a first energy response and the detection crystal units 23 having a second energy response are, at least partially, alternatively arranged along the first direction, in a mode of single energy processing, the spatial sampling locations for detecting the X-ray are increased, compared to the conventional arrangement in which the detection crystal units having a second energy response and the detection crystal units having a first energy response are arranged to be aligned with each other. A part of the X-ray emitted from the X-ray source is acquired by either of the detection crystal units 22 having a first energy response and the detection crystal units 23 having a second energy response that are alternatively arranged, and the rest of the X-ray is acquired by the detection crystal units having a first energy response and the detection crystal units having a second energy response that are aligned with each other. Then, all the acquired data signals are used for CT image reconstruction of the scanned object, so that spatial resolution can be enhanced. Furthermore, since the number of the detection crystal units 23 having a second energy response is not increased, manufacturing cost for the detector device will not be increased.

Figure 3A:
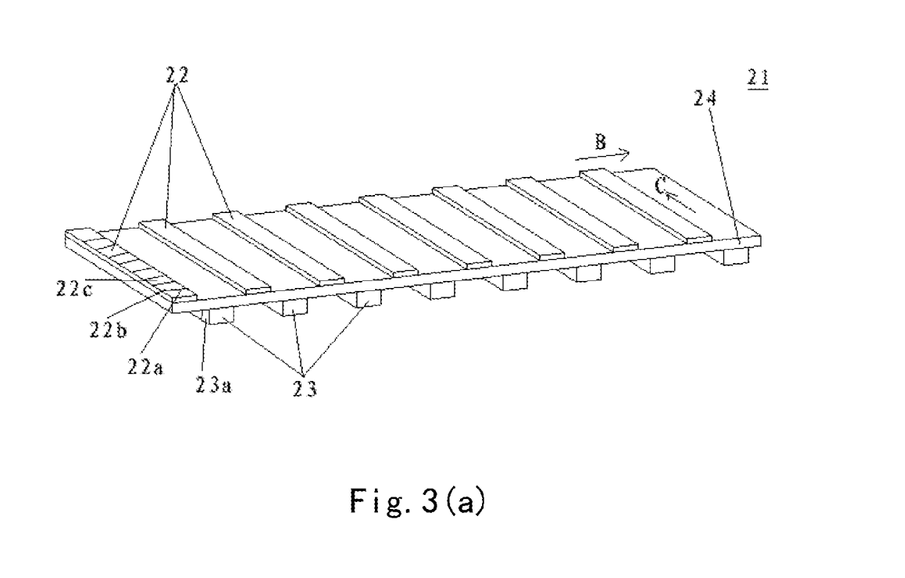
FIGS. 3a-3e show exemplary arrangements of the detection crystal units having a first energy response and the detection crystal units having a second energy response in the detector assemblies of the detector device according to the present disclosure.
Figure 3B:
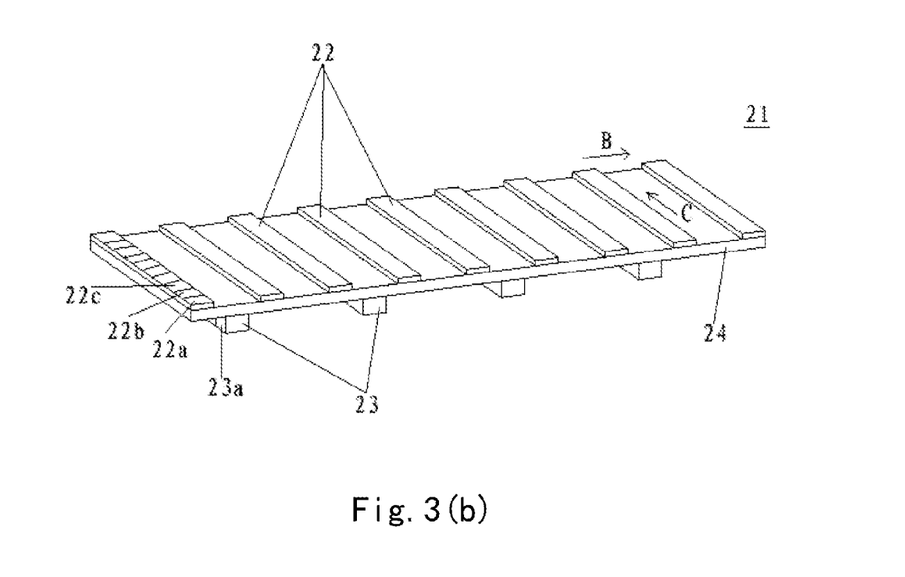
Figure 3C:
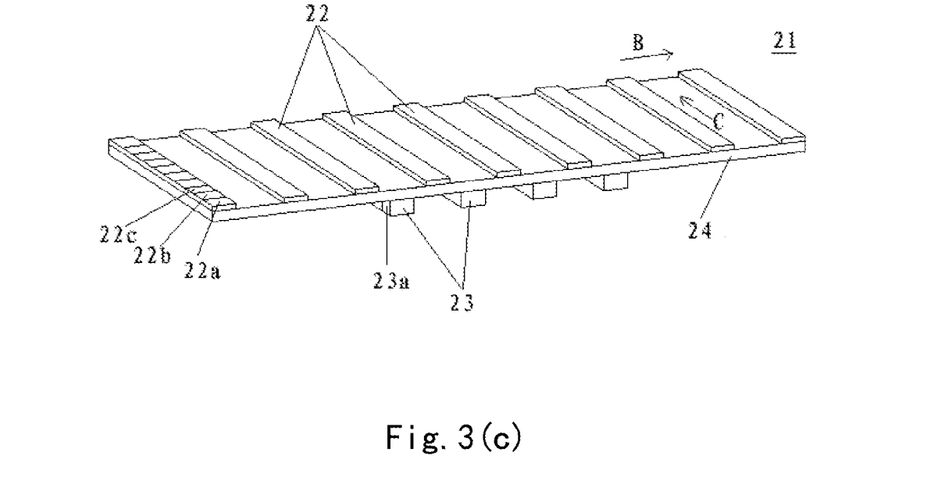
Figure 3D:
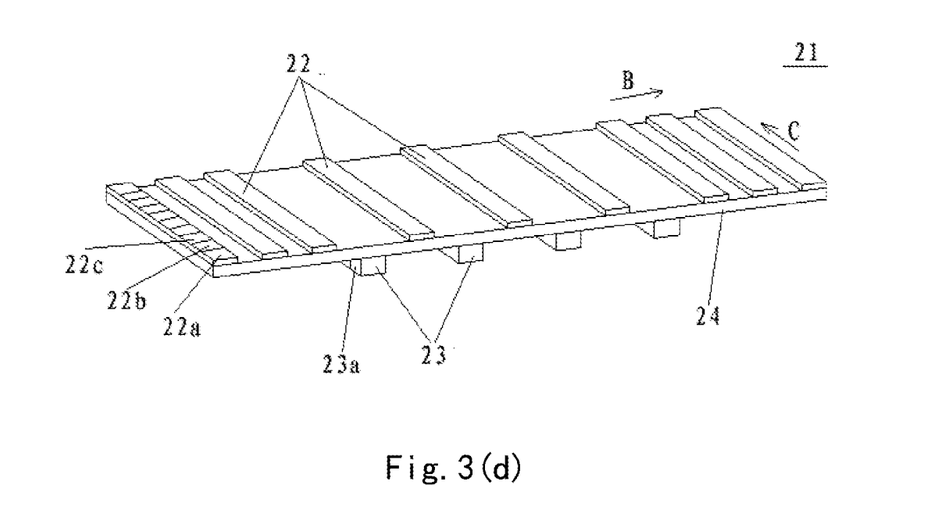

In a specific embodiment, the number of the detection crystal units 22 having a first energy response may be equal to that of the detection crystal units 23 having a second energy response, for example, as shown in FIG. 3(a). The number of the detection crystal units 22 having a first energy response may be equal to that of the detection crystal units 23 having a second energy response, for example, as shown in FIGS. 3(b)-3(d). Since the cost of the detection crystal having a first energy response is much lower than that of the detection crystal having a second energy response, spatial resolution for CT image reconstruction can be enhanced by increasing the number of the detection crystal units having a first energy response, and thus the manufacturing cost of the detector device will not be evidently increased.

The detection crystal units 22 having a first energy response and the detection crystal units 23 having a second energy response may be arranged in an entirely alternative manner, that is, any of the detection crystal units 22 having a first energy response is not aligned with any of the detection crystal units 23 having a second energy response, as shown in FIGS. 3(a)-3(d). Such arrangement means that in the mode of single energy processing, the spatial sampling locations for X-ray detection are further increased by alternatively arranging all the detection crystal units having a first energy response and a second energy response, without changing the total number of the detection crystal units (i.e., without increasing the total manufacturing cost), thereby further enhancing the spatial resolution for CT image reconstruction.

Figure 3E:
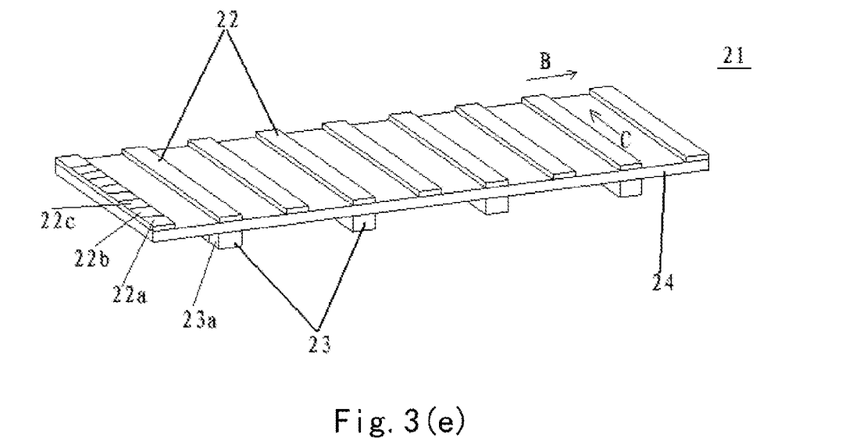

FIG. 3(e) shows an another exemplary arrangement of the detection crystal units 22 having a first energy response and the detection crystal units 23 having a second energy response in the detector assembly 21 of the detector device 20 according to the present disclosure. In this exemplary arrangement, each detector assembly 21 comprises at least two detection crystal units 22 having a first energy response arranged along the first direction at intervals, and each detection crystal unit 22 having a first energy response comprises at least one detection crystals 22a, 22b, 22c . . . having a first energy response arranged along the second direction. The first direction is parallel to the transporting direction of the scanned object. The second direction is perpendicular to the first direction. The detector assembly 21 also comprises at least one detection crystal units 23 having a second energy response arranged along the first direction at intervals, and each detection crystal unit 23 having a second energy response comprises at least one detection crystals 23a . . . having a second energy response arranged along the second direction. The second energy is higher than the first energy. The number of the detection crystal units 23 having a second energy response is less than that of the detection crystal units 22 having a first energy response. When viewed from an incidence direction of the X-ray, some of the at least two detection crystal units 22 having a first energy response correspond to and are arranged to be aligned with respective detection crystal units of the at least one detection crystal units 23 having a second energy response.

In this way, on one hand, sharpness of three-dimension images can be enhanced by increasing the number of the detection crystal units 22 having a first energy response; on the other hand, since the number of the detection crystals required for meeting accuracy requirements of substance identification is much less than the number of the detection crystals required for meeting sharpness requirements of three-dimension images, providing a small amount of the detection crystal units 23 having a second energy response will not bring any adverse influence on substance identification. Therefore, detection cost can be optimized, and a higher spatial resolution for CT image reconstruction can be ensured while meeting accuracy requirements of substance identification.

As exemplarily shown in FIGS. 3(*a*)-(*e*), in an embodiment, the detector device further comprises a mounting plate 24. The detection crystal units having a first energy response are arranged on a side of the mounting plate 24 in such manner that the detection crystal units having a first energy response are arranged along the first direction at intervals, and the detection crystal units having a second energy response are arranged on the other side of the mounting plate 24 in such manner that the detection crystal units having a second energy response are arranged along the first direction at intervals. Alternatively, the at least one detection crystal units having a first energy response and the at least one detection crystal units having a second energy response are mounted on the same or different sides of different mounting plates. In an embodiment, the mounting plate 24 may be a printed circuit board, and a circuit corresponding to the detection crystal units is provided on the printed circuit board.

In a preferred embodiment, an incidence surface of the detection crystal unit in the detector assembly as shown in FIGS. 3(*a*)-(*e*) may be provided with a filtering layer (not shown), such as a copper layer, for adjusting an energy response of the detection crystal unit. In an embodiment, the X-ray source is a single light source or a distributed multi-beam source.

An improved arrangement of detector assemblies was disclosed in Chinese Patent Application No. 201210350516.X (CT SECURITY INSPECTION SYSTEM FOR BAGGAGE AND DETECTOR ARRANGEMENT THEREOF) owned by the applicant of the present application. The plurality of detector assemblies described in the present disclosure may be arranged in the arrangement disclosed in the Chinese Patent Application No. 201210350516.X, so as to reduce the size of the CT security inspection system and to improve scan efficiency. Specifically, the plurality of detector assemblies 21 may be arranged on a circular arc-shaped support centered at a center of the scanning tunnel or on an approximate circular arc-shaped support consisting of a plurality of straight members. However, it should be noted that the plurality of detector assemblies may be arranged on a circular arc-shaped support centered at the X-ray source or an approximate circular arc-shaped support consisting of a plurality of straight members in a conventional way.

In an embodiment, the plurality of detector assemblies may be arranged on the circular arc-shaped or approximate circular arc-shaped support in a spiral manner, so that a detection path for detecting the scanned object is a spiral path when the scanned object is transported to pass through a scanning plane. The spiral path is defined as a spatial path through which a fixed point (such as a light source and the like) on the slip-ring passes when the scanned object is transported to pass through the scanning plane, with the scanned object being taken as a resting reference. Specifically, referring to FIG. 2, in the plurality of detector assemblies, for example, in the order of from left to right/from right to left, one detector assembly is moved toward a page-in direction/a page-out direction in sequence by a distance relative to another adjacent detector assembly.

In an embodiment, the dual energy CT system according to the present disclosure further comprises a data processing module (not shown). The data processing module may be integrated on the dual energy CT system, or may be separately provided. The data processing module is configured to perform a first data processing and a second data processing. In the first data processing, a single energy processing mode is used, and data signals from the detection crystal units 23 having a second energy response, data signals from the detection crystal units 22 having a first energy response and data signals from a unit block formed by the detection crystal units 22 having a first energy response and the detection crystal units 23 having a second energy response that are aligned with each other are not distinguished. All the acquired data signals are used to reconstruct CT images of the scanned object, such as baggage, so as to detect prohibited articles, such as knives or weapon. In the second data processing, a dual energy processing mode is used, and the acquired data signals are decomposed into data signals from the at least one detection crystal units 22 having a first energy response and data signals from the at least one detection crystal units 23 having a second energy response by a dual energy decomposition technique. Then, the decomposed data signals are used for reconstruction to obtain attenuation coefficient images, electron density images and atomic number images of the scanned article in X-ray scanning with different energies, so as to identify substance and detect prohibited articles, such as drugs or explosives.

As one skilled in the art can know, in a case where the detection crystal units 22 having a first energy response and the detection crystal units 23 having a second energy response are arranged in an entirely alternative manner or are arranged in a partially alternative manner, the dual energy decomposition cannot be directly realized because some of the detection crystal units having a first energy response and a second energy response are not aligned with each other. Accordingly, the inventors propose that the data processing module can be configured to employ interpolation algorithms to obtain dual energy projection data which correspond to an alignment arrangement and then reconstruct the electron density images and the atomic number images in the case where the detection crystal units 23 having a second energy response and the detection crystal units 22 having a first energy response are, at least partially, alternatively arranged, during performing the second data processing. With such configuration, the above-mentioned problem that the dual energy decomposition cannot be directly realized due to misalignment of the detection crystal units 23 having a second energy response and the detection crystal units 22 having a first energy response can be solved.

Figure 4:
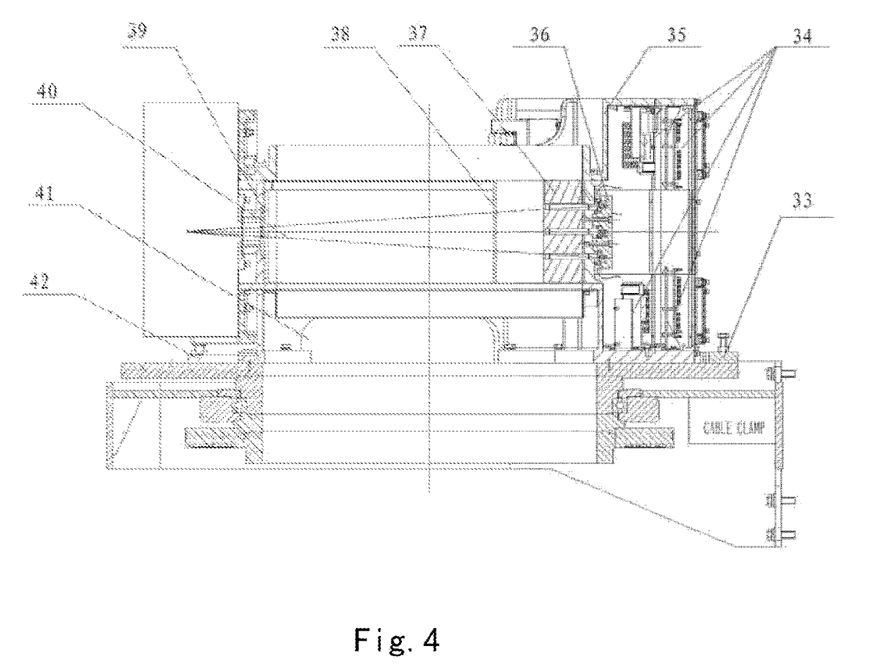
FIG. 4 is a top view showing a schematic structure view of the detector device.

FIG. 4 is a top view showing a schematic structure view of the dual energy CT system according to the present disclosure. The dual energy CT system further comprises the first collimator 9 and the second collimator 10. The first collimator 9 includes collimator grids 39 for decomposing the ray emitted by the X-ray source 8 and controlling energy intensity of X-ray beams outputted from each of the grids.

The second collimator 10 includes grids 37 for shielding the X-ray incident onto the detector assemblies such that the X-ray arriving at a detector crystal receiving face can be ensured to come from a major face of the detection crystal, instead of being scattered by edges of the detector crystal receiving face. As shown in FIG. 4, the grids 39 of the first collimator 9 include at least two partitions for decomposing the ray emitted by the X-ray source 8 into two or more sector ray beams. Further, as shown in FIG. 4, along the direction of the scanning tunnel 2 or 6, the respective decomposed sector ray beams correspond to respective receiving faces of the plurality of detection crystal units 22 and 23 so as to synchronously acquire data from a plurality of columns of detectors along the direction of the scanning tunnel 2 or 6. The plurality of detector assemblies 21 may consist of a plurality of detector crystal units mounted within a detector mounting case 35 through a detector crystal mounting bracket. The detector mounting case is sealed to reduce disturbance on performance of the detector crystals caused by light, dust and environmental humidity. The detector mounting case 35 is mounted on the CT gantry by an attachment support 42. In order to reduce shielding of the ray beams in the main direction while ensuring sealing and shading, a dustproof shadow shield 38 is mounted at a position in front of the detector crystal receiving faces, towards the target of the X-ray source. Preferably, the thickness of the dustproof shadow shield 38 is not greater than 3 mm. The dustproof shadow shield is made of lightweight material, including but not limited to Teflon, plastics, bakelite and aluminum foil. In the preferred embodiment, the collimator grids 39 of the first collimator are embodied as one or more dotted fitting curves related to distribution of ray energy, wherein slits of some of the grids in the middle are relatively narrow while slits of some of the grids in the margin are relatively wide, such that energy intensities reaching the different detector crystal receiving faces are substantially same. In a specific embodiment, the collimator grids 39 of the first collimator is provided with a plurality of slits, at least two, e.g., three as shown in FIG. 4.

Brief description on specific operation of the dual energy CT system according to the present disclosure will be introduced in the followings. Through the scanning entrance tunnel 2, the object to be scanned (not shown), such as baggage, is transported into the dual energy CT system. Meanwhile, a light barrier at the entrance is actuated, and with acquisition commands issued by a system controlling module, the slip-ring 3 is driven by the slip-ring driving motor 14 to rotate and hence the gantry 5 starts to rotate along with rotation of the slip-ring 3. The X-ray emitted by the X-ray source 8 in the CT system passes through the first collimator 9 which is used as a front energy collimating device, and the latter splits the energy ray into a plurality of columns of sector X-ray beams. Then, the detector assemblies 21 begin to acquire the data on these X-ray beams. Finally, the acquired data is used for reconstruction by the data processing module. Specifically, the data processing module is configured to perform a first data processing and a second data processing. In the first data processing, a single energy processing mode is used, and all the acquired data signals are used to reconstruct CT images of the scanned object, such as baggage, to obtain the structure and the shape images of the scanned object, thereby detecting prohibited articles, such as knives or weapon. In the second data processing, a dual energy processing mode is used, and the acquired data signals are decomposed into data signals from the at least one detection crystal units 22 having a first energy response and data signals from the at least one detection crystal units 23 having a second energy response by, for example, a conventional dual energy decomposition technique. Then, the decomposed data signals are used for reconstruction to obtain attenuation coefficient images, electron density images and atomic number images of the scanned article in X-ray scanning with different energies, so as to identify substance and detect prohibited articles, such as drugs or explosives. In a preferred embodiment, in the second data processing, interpolation algorithms are employed to obtain dual energy projection data which correspond to an alignment arrangement and then reconstruct the electron density images and the atomic number images in the case where the detection crystal units 23 having a second energy response and the detection crystal units 22 having a first energy response are, at least partially, alternatively arranged.

Although several exemplary embodiments have been shown and described, the present invention is not limited to those and it would be appreciated by those skilled in the art that various changes or modifications may be made in these embodiments without departing from the principles and spirit of the disclosure, which should fall within the scope of the present invention. The scope of the invention is defined by the claims and their equivalents.

What is claimed is:

1. A detector device for a dual energy CT system, wherein the dual energy CT system comprises a scanning tunnel through which an object to be scanned enters/exits the dual energy CT system along a transporting direction, an X-ray source provided at a side of the scanning tunnel, and a gantry provided at an opposite side of the scanning tunnel and on which the detector device is mounted, and wherein the detector device comprises a plurality of detector assemblies and a mounting plate, each detector assembly comprising:
   at least two detection crystal units having a first energy response arranged along a first direction at intervals and arranged on a side of the mounting plate, and each detection crystal unit having the first energy response comprises at least one detection crystal having the first energy response arranged along the second direction, wherein the first direction is parallel to the transporting direction, and the second direction is perpendicular to the first direction in a plane of the mounting plate; and
   at least one detection crystal unit having a second energy response arranged along the first direction at intervals and arranged on the other side of the mounting plate, and each detection crystal unit having the second energy response comprises at least one detection crystal having the second energy response arranged along the second direction, wherein the second energy is higher than the first energy;
   wherein the number of the detection crystal units having the second energy response is less than that of the detection crystal units having the first energy response, and when viewed from an incidence direction of the X-ray, some of the at least two detection crystal units having the first energy response correspond to and are arranged to be aligned in a third direction perpendicular to the first direction and the second direction with respective detection crystal units of the at least one detection crystal unit having the second energy response.

2. The detector device for the dual energy CT system according to claim 1, wherein the plurality of detector assemblies are arranged on a circular arc-shaped support centered at a center of the scanning tunnel or the X-ray source or on an approximate circular arc-shaped support consisting of a plurality of straight members.

3. The detector device for the dual energy CT system according to claim 2, wherein the plurality of detector assemblies are arranged on the circular arc-shaped or approximate circular arc-shaped support in a spiral manner, so that a detection path for detecting the scanned object is a spiral path when the scanned object is transported to pass through a scanning plane.

4. The detector device for the dual energy CT system according to claim 1, wherein incidence surfaces of the detection crystal units having the first energy response and/or the detection crystal units having the second energy response are provided thereon with filtering layers for adjusting the energy response of the detection crystal units.

5. The detector device for the dual energy CT system according to claim 1, wherein the at least one detection crystal unit having the first energy response and the at least one detection crystal unit having the second energy response are mounted on different sides of different mounting plates.

6. The detector device for the dual energy CT system according to claim 1, wherein the X-ray source is a single light source or a distributed multi-beam source.

7. A dual energy CT system, comprising:
a scanning tunnel through which an object to be scanned enters/exits the dual energy CT system along a transporting direction;
an X-ray source provided at a side of the scanning tunnel; and
the gantry provided at an opposite side of the scanning tunnel;
wherein the detector device according to claim 1 is mounted on the gantry.

8. The dual energy CT system according to claim 7, further comprising:
an acquisition module for acquiring data signals from the plurality of detector assemblies; and
a control module for controlling radiation emission of the X-ray source and the data signal acquisition operation,
wherein the control module and the acquisition module are mounted within the same gantry.

9. The dual energy CT system according to claim 8, further comprising a data processing module, and the data processing module is configured to perform a first data processing and a second data processing,
wherein in the first data processing, a single energy processing mode is used, and all the acquired data signals are used to reconstruct CT images of the scanned object; in the second data processing, a dual energy processing mode is used, and the acquired data signals are decomposed into data signals from the at least one detection crystal having a first energy response and data signals from the at least one detection crystal having a second energy response, and the decomposed data signals are used for reconstruction to obtain attenuation coefficient images, electron density images and atomic number images of the scanned article in X-ray scanning with different energies.

10. The dual energy CT system according to claim 9, wherein the data processing module is configured to, in the second data processing, employ interpolation algorithms to obtain dual energy projection data which correspond to an alignment arrangement and then perform reconstruction of attenuation coefficient images, electron density images and atomic number images in X-ray scanning with different energies in the case where the detection crystal units having a second energy response and the detection crystal units having a first energy response are alternatively arranged.

* * * * *